(12) United States Patent
Chen et al.

(10) Patent No.: US 10,039,837 B2
(45) Date of Patent: Aug. 7, 2018

(54) MULTI-ARM POLYETHYLENE GLYCOL-AZIDO DERIVATIVE

(71) Applicant: JENKEM TECHNOLOGY CO., LTD. (TIANJIN), Tianjin (CN)

(72) Inventors: Xiaomeng Chen, Tianjin (CN); Meina Lin, Tianjin (CN); Xuan Zhao, Tianjin (CN)

(73) Assignee: JENKEM TECHNOLOGY CO., LTD. (TIANJIN), Tianjin (CN)

( * ) Notice: Subject to any disclaimer, the term of this patent is extended or adjusted under 35 U.S.C. 154(b) by 0 days.

(21) Appl. No.: 15/170,839

(22) Filed: Jun. 1, 2016

(65) Prior Publication Data

US 2016/0271266 A1    Sep. 22, 2016

Related U.S. Application Data

(63) Continuation of application No. PCT/CN2014/092737, filed on Dec. 2, 2014.

(30) Foreign Application Priority Data

Dec. 2, 2013 (CN) .......................... 2013 1 0643900

(51) Int. Cl.
*C08G 65/333* (2006.01)
*C08G 65/337* (2006.01)
*C08G 65/334* (2006.01)
*A61K 47/48* (2006.01)
*C08G 65/325* (2006.01)
*C08G 65/332* (2006.01)

(52) U.S. Cl.
CPC ...... *A61K 47/48215* (2013.01); *C08G 65/325* (2013.01); *C08G 65/332* (2013.01); *C08G 65/333* (2013.01); *C08G 65/337* (2013.01); *C08G 65/3346* (2013.01); *C08G 65/33327* (2013.01); *C08G 65/33331* (2013.01); *C08G 65/33337* (2013.01); *C08G 65/33396* (2013.01); *C08G 2650/30* (2013.01)

(58) Field of Classification Search
CPC ............ A61K 47/48215; C08G 65/325; C08G 65/332; C08G 65/333; C08G 65/33327; C08G 65/33396; C08G 65/3346; C08G 65/337; C08G 2650/30; C08G 65/33331; C08G 65/33337
USPC ...................................................... 548/521
See application file for complete search history.

(56) References Cited

U.S. PATENT DOCUMENTS

2012/0077988 A1*  3/2012  Yamamoto ......... C07D 207/452
                                                                548/462

* cited by examiner

*Primary Examiner* — Kristin A Vajda
(74) *Attorney, Agent, or Firm* — Flener IP & Business Law; Zareefa B. Flener

(57) ABSTRACT

Provided is a multi-arm polyethylene glycol-azido derivative of general formula I, wherein R is a central molecule, which is selected from a polyhydroxy structure, a polyamino structure or a polycarboxyl structure; n is the number of branches or arms, $n \geq 3$; PEG is the same or different $-(CH_2CH_2O)_m-$, the average value of m being an integer from 3 to 250; X is a linking group of a azido end group; k is the number of the branches having the azido end group; F is selected from the group consisting of amino, carboxyl, sulfhydryl, ester group, maleic imide group and acrylic group; and Y is a linking group of an end group F.

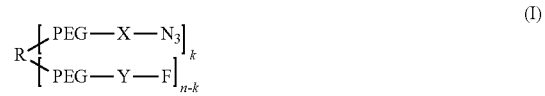

18 Claims, No Drawings

MULTI-ARM POLYETHYLENE GLYCOL-AZIDO DERIVATIVE

CROSS-REFERENCE TO RELATED APPLICATION

The application is a continuation of PCT/CN2014/092737 (filed on Dec. 2, 2014), which claims priority from CN Patent Application Serial No. 201310643900.3 (filed on Dec. 2, 2013), the entire contents of which are incorporated herein by reference for all purposes.

FIELD OF THE INVENTION

The present invention relates to a multi-arm polyethylene glycol active derivative, more particularly, to a multi-arm polyethylene glycol active derivative having azido-chain-terminated and a preparation method thereof.

BACKGROUND OF THE INVENTION

The polyethylene glycol is an extremely versatile polyether high molecular weight compounds, it can be used in many fields such as medicine, health, food, chemical, etc. Polyethylene glycol can be dissolved in water and many solvents and the polymer has excellent biocompatibility, can be dissolved in tissue fluid in vivo, can be rapidly excreted from the body without any toxic side effects.

In application of polyethylene glycol, end group plays a decisive role, different end groups of the polyethylene glycol has a different use. The polyethylene glycol polymeric chain segment is not limited to the terminal hydroxyl group, polyethylene glycol active derivative obtained through the introduction of other functionalized end groups such as amino, carboxyl, aldehyde group and the like, can greatly broaden the range of applications of polyethylene glycol, making it has a broad application prospect in organic synthesis, peptide synthesis, polymer synthesis and sustained release or controlled release of drugs, targeting administration, etc.

Polyethylene glycol (PEG) active derivative has been reported in many document. The U.S. Pat. No. 5,672,662 described the preparation of linear PEG propionic acid and linear PEG butyric acid, and N-hydroxy succinimide esters thereof. The U.S. Pat. No. described a u-shaped structure of PEG derivative.

Azide not only have important physiological activity, such as azido nucleotides (AZT), is a preferred drug available for treatment of AIDS currently, but also have a wide range of reaction activity, as can be reduced to the amino, can occur 1,3-dipolar cyclo addition reaction with an alkyne, can occur Curtius reaction. Azido-terminated polymer obtained by reducing terminal azido group as a polymeric carrier plays an important role in the liquid phase synthesis of peptide.

Patent document WO 2011075953 A1 describes a novel multi-arm polyethylene glycol having different type of active groups, which formed by the polymerization of ethylene oxide, and an oligomeric pentaerythritol as the initiator. The active end group is selected from the group consisting of hydroxyl, amino, sulfhydryl, carboxyl, ester group, aldehyde group, acrylic and maleic imide group, it does not disclose active end group may be azido group.

Non-patent document "synthesis and characterization of azido-terminated polyethylene glycol" (Xiaohong Wang et. al., Acta Polymerica Sinica, June 2000, issue 3) discloses a synthesis method of a high molecular weight azido-terminated polyethylene glycol, however, the prepared polymer is a linear polyethylene glycol, and only loaded with azido groups, and can not be introduced into the other active groups.

To overcome the deficiencies of the prior art, the present invention provides a multi-arm polyethylene glycol-azido active derivative.

SUMMARY OF THE INVENTION

One objective of the present invention is to provide a multi-arm polyethylene glycol-azido active derivative, compared with a linear polyethylene glycol, the multi-arm polyethylene glycol has a plurality of groups, further has a plurality of introduction points of functional groups, may load a plurality of different active end groups, solve the problems of a poor flexibility-of-use and a smaller application-scoped of polyethylene glycol-azido derivative.

Another object of the present invention is to provide a multi-arm polyethylene glycol-azido active derivative, which can be reacted with other types of polymer, used for the preparation of gel, enabled lower reaction conditions and shorten the gel formation time.

Another object of the present invention is to provide a series of different structures of multi-arm polyethylene glycol-azido active derivatives, solve the problems that the active ingredient release speed can not control when a multi-arm polyethylene glycol-azido active derivative forming a gel.

One aspect of the present invention provides a multi-arm polyethylene glycol-adizo derivative having a structure of a general formula I:

Wherein:
R is a central molecule selected from the group consisting of a polyhydroxy structure,
a polyamino structure and a polycarboxyl structure;
n is the number of branches or the number of arms, n≥3;
PEG is the same or different —$(CH_2CH_2O)_m$—, m is an integer of average value of 3-250;
X is a linking group of a azido end group, selected from the group consisting of $C_{1-12}$ alkyl, aryl alkyl, ester group, carbonate group, amide group, amide ester group, ether group, urethane group;
K is the number of the branches having the azido end group, 2≤k≤n;
F is an active end group different from the azido, selected from the group consisting of amino, carboxyl, sulfhydryl, ester group, maleic imide group and acrylic group;
Y is a linking group of an end group F, selected from the group consisting of $(CH_2)_i$, $(CH_2)_iNH$, $(CH_2)_iOCOO$—, $(CH_2)_iOCONH$—, $(CH_2)_iNHCOO$—, $(CH_2)_iNHCONH$—, $OC(CH_2)_iCOO$—, $(CH_2)_iCOO$—, $(CH_2)_iCONH$; i is an integer of 1-10.

In the present invention, in the multi-arm polyethylene glycol-azido derivative of general formula I, R is pentaerythritol or polypentaerythritol structure, methyl glucoside, sucrose, glycerol or polyglycerol structure, and more particularly, R is preferably

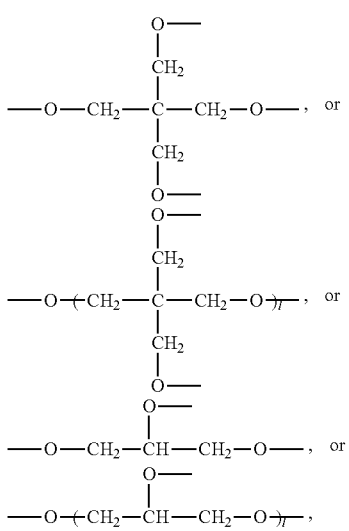

Wherein 1 is an integer of ≥1 and ≤10, preferably 1 is an integer of ≥1 and ≤6, especially preferably 11 is an integer of ≥1 and ≤4, in one embodiment of the present invention, 1 may preferably be 1, 2, 3, 4, 5 or 6.

In the present invention, in the multi-arm polyethylene glycol-azido derivative of general formula I, n is the number of branches or the number of arms, n≥3, preferably, 3≤n≤22, more preferably 3≤n≤14, and most preferably 3≤n≤6.

In the present invention, in the multi-arm polyethylene glycol-azido derivative of general formula I, k is the number of the branches having the azido end group, 2≤k≤n, preferably 2≤k≤16, more preferably 2≤k≤6, in an embodiment of the present invention k may be 2, 4, 6, 8, 10, 12, 14 or 16.

In one embodiment of the present invention, k=n, the multi-arm polyethylene glycol-azido derivative having a structure of a general formula II:

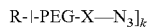

R-I-PEG-X—N₃]ₖ          (II);

In one embodiment of the present invention, n−k=2, the multi-arm polyethylene glycol-azido derivative having a structure of a general formula III:

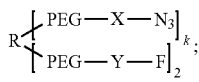

(III)

Wherein, preferably 2≤k≤16, more preferably 2≤k≤6, in an embodiment of the present invention k may be 2, 4, 6, 8, 10, 12, 14 or 16.

In the present invention, in the multi-arm polyethylene glycol-azido derivative of general formula I, m is an integer of average value of 3-250, preferably m is an integer of 68-250, more preferably m is an integer of 68-227.

In the present invention, in the multi-arm polyethylene glycol-azido derivative of general formula I, X is a linking group of a azido end group, selected from the group consisting of $C_{1-12}$ alkyl, aryl alkyl, ester group, carbonate group, amide group, amide ester group, ether group, urethane group; preferably selected from the group consisting of $(CH_2)_i$, $(CH_2)_iNH$, $(CH_2)_iOCOO$—, $(CH_2)_iOCONH$—, $(CH_2)_iNHCOO$—, $(CH_2)_iNHCONH$—, $OC(CH_2)_iCOO$—, $(CH_2)_iCOO$—, $(CH_2)_iCONH$, $(CH_2)_iCOO$—; more preferably X is $(CH_2)_i$, $(CH_2)_iNH$, $(CH_2)_iCOO$—, $(CH_2)_iCO$—.

In the present invention, in the multi-arm polyethylene glycol-azido derivative of general formula I, Y is a linking group of an end group F, selected from the group consisting of $(CH_2)_i$, $(CH_2)_iNH$, $(CH_2)_iOCOO$—, $(CH_2)_iOCONH$—, $(CH_2)_iNHCOO$—, $(CH_2)_iNHCONH$—, $OC(CH_2)_iCOO$—, $(CH_2)_iCOO$—, $(CH_2)_iCONH$; preferably Y is $(CH_2)_i$, $(CH_2)_iNH$, $(CH_2)_iOCOO$—, $(CH_2)_iOCONH$—, $(CH_2)_iNHCOO$—, $(CH_2)_iNHCONH$—, $OC(CH_2)_iCOO$—, $(CH_2)_iCOO$—, $(CH_2)_iCONH$, $(CH_2)_iCOO$—; more preferably Y is $(CH_2)_i$, $(CH_2)_iNH$, $(CH_2)_iCOO$—, $(CH_2)_iCO$—.

In the present invention, in the multi-arm polyethylene glycol-azido derivative of general formula I, i is an integer of 1-10 in X and Y, preferably i is an integer of 1-5, more preferably i is an integer of 1-3, in one embodiment of the present invention, i is 1, 2, 3, 4 or 5.

In the present invention, in the multi-arm polyethylene glycol-azido derivative of general formula I, F is an active end group different from the azido, selected from the group consisting of amino, carboxyl, sulfhydryl, ester group, maleic imide group and acrylic group; preferably F is —NH₂, —COOH, —OCH₃,

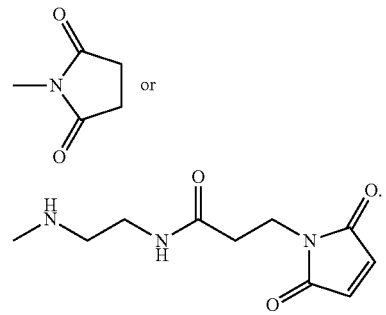

In one embodiment of the present invention, the multi-arm polyethylene glycol-azido derivative having a structure of a general formula I of the present invention is shown as:

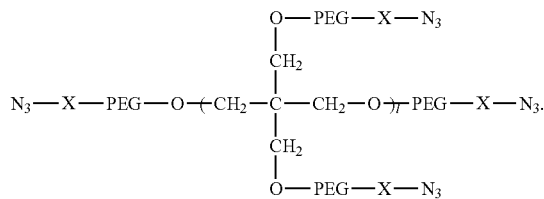

In one embodiment of the present invention, the multi-arm polyethylene glycol-azido derivative having a structure of a general formula I of the present invention is shown as:

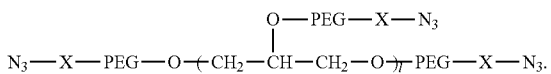

In particular embodiments of the present invention, the multi-arm polyethylene glycol derivative has a molecular weight of 1,000-80,000 Da, in a preferred embodiment of the present invention, the multi-arm polyethylene glycol has a molecular weight of 3,000-20,000 Da, in a more preferred embodiment, the multi-arm polyethylene glycol has a molecular weight of 3,000 to about 10,000 Da, in a most preferred embodiment, the multi-arm polyethylene glycol may have a molecular weight of 3,000 Da, 5,000 Da, 10,000 Da, 20,000 Da.

In one particular embodiment, the multi-arm polyethylene glycol-azido derivative is a multi-arm polyethylene glycol-azido-mono-acetic acid having a structure of a general formula V:

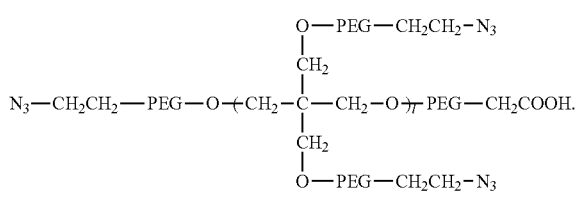

In one particular embodiment, the multi-arm polyethylene glycol-azido derivative is a multi-arm polyethylene glycol-azido-multi-acetic acid having a structure of a general formula VI:

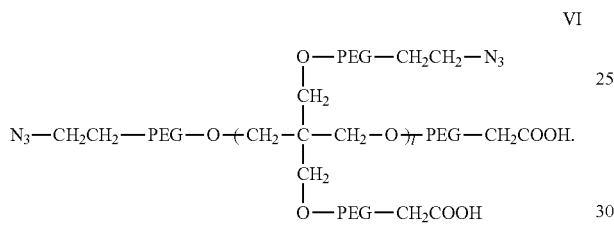

In one particular embodiment, the multi-arm polyethylene glycol-azido derivative is a multi-arm polyethylene glycol-azido-mono-NHS ester having a structure of a general formula VII:

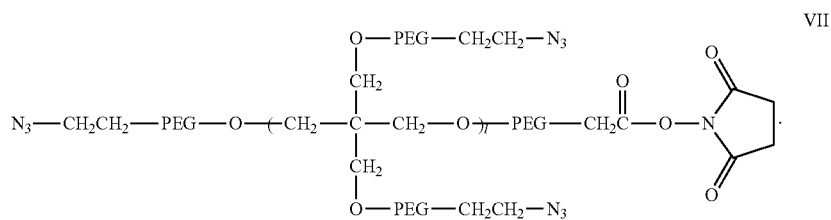

In one particular embodiment, the multi-arm polyethylene glycol-azido derivative is a multi-arm polyethylene glycol-azido-multi-NHS ester having a structure of a general formula VIII:

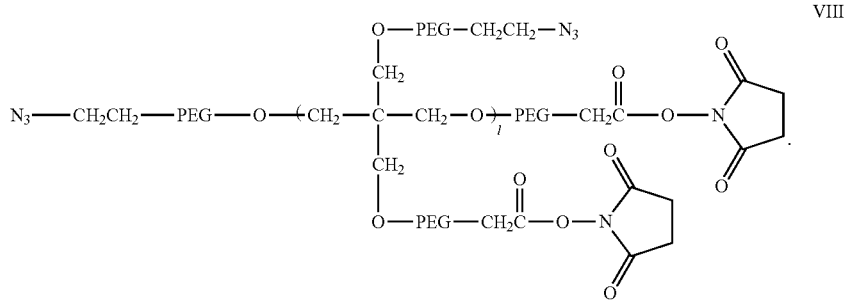

In one particular embodiment, the multi-arm polyethylene glycol-azido derivative is a multi-arm polyethylene glycol-azido-mono-amine having a structure of a general formula IX:

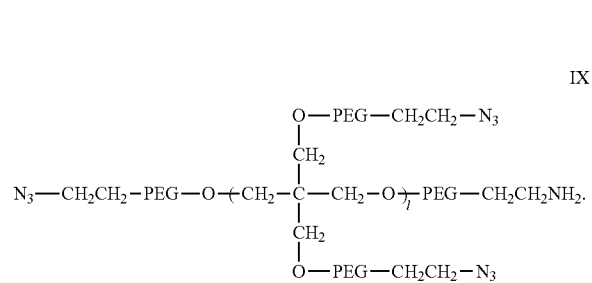

In one particular embodiment, the multi-arm polyethylene glycol-azido derivative is a multi-arm polyethylene glycol-azido-multi-amine having a structure of a general formula X:

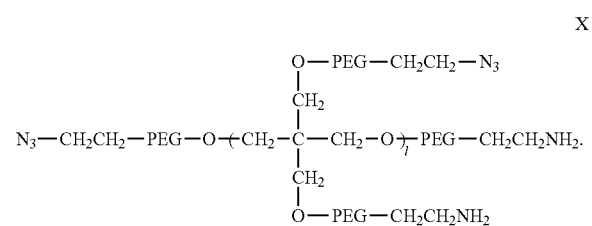

In one particular embodiment, the multi-arm polyethylene glycol-azido derivative is a multi-arm polyethylene glycol-azido-mono-maleimide having a structure of a general formula XI:

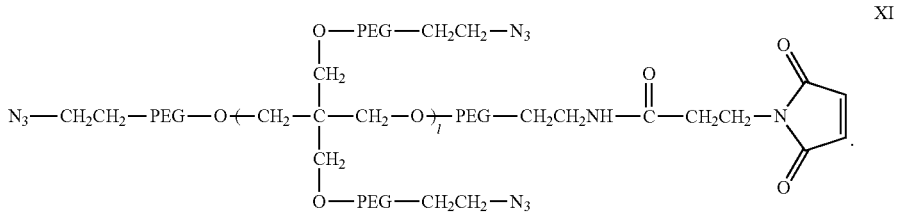

XI

In one particular embodiment, the multi-arm polyethylene glycol-azido derivative is a multi-arm polyethylene glycol-azido-multi-maleimide having a structure of a general formula XII:

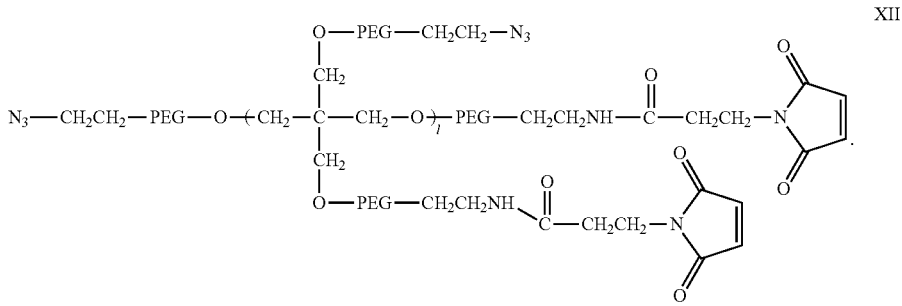

XII

Another aspect of the present invention provides a method of preparing a multi-arm polyethylene glycol-azido derivative of general formula I, comprising: reacting a multi-arm polyethylene glycol with methanesulfonyl chloride to yield a multi-arm polyethylene glycol sulfonic acid ester, reacting a multi-arm polyethylene glycol sulfonic acid ester with sodium azide to yield the multi-arm polyethylene glycol-azido derivative.

Another aspect of the present invention provides a method of preparing a multi-arm polyethylene glycol-azido derivative of general formula I, comprising: selecting a compound having two active groups, reacting a multi-arm polyethylene glycol with one of the active end groups to introduce a linking group X, then introducing an azido-terminated through another active end group.

Another aspect of the present invention provides a method of preparing a multi-arm polyethylene glycol-azido derivative of general formula I, comprising: reacting an azido compound (P—X—N$_3$) having a active group P with the hydroxyl-terminated of a multi-arm polyethylene glycol to yield a azido derivative. Wherein, the active group P is selected from the group consisting of amino, carboxyl, sulfhydryl, ester group, maleic imide group and acrylic group; preferably P is —NH$_2$, —COOH, —OCH$_3$,

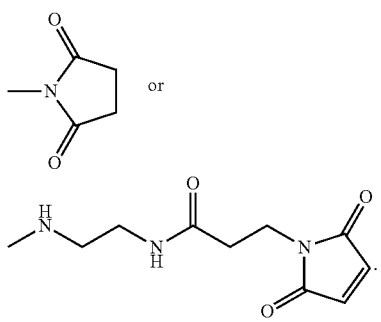

In one embodiment of the present invention, the method of preparing a multi-arm polyethylene glycol-azido derivative of general formula I, including:

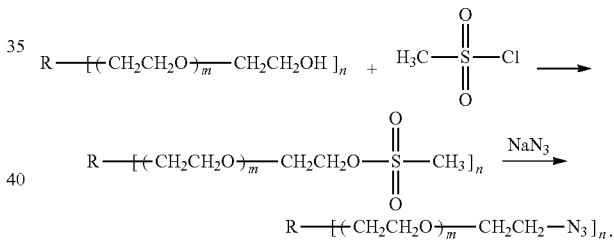

The multi-arm polyethylene glycol-azido derivative of general formula I of the present invention may be used to conjugated with protein, peptide or drug active small molecule, may increase the targeting ability and drug efficacy, reduce the toxicity. The protein, peptide or drug active small molecule include, but are not limited to, analgesics and anti-inflammatory agents, antacids, anthelmintics, anti-arrhythmia agents, antibacterial agents, anticoagulants, antidepressants, antidiabetic agents, antidiarrheal agents, antiepileptic agents, anti-fungal agents, anti-gout agents, antihypertensive drugs, anti-malarials, anti-migraine agents, anti-muscarinic agents, anti-tumor agents and immunosuppressive agents, anti-protozoal agents, anti-rheumatic agents, anti-thyroid agents, anti-viral agents, anti-anxiety agents, sedative agents, ophthalmic drugs and tranquilizers, β-receptor blocking agents, cardiac-contraction agents, corticosteroids, cough suppressants, cytotoxic agents, decongestants, diuretics, enzymes, anti-parkinsonian agents, gastrointestinal agents, histamine receptor antagonists, grease modulating agents, local anesthetics, neuromuscular blocking agents, nitrate and anti-anginal agents, nutritional agents, narcotic analgesics, oral vaccines, proteins, peptides and recombinant drugs, sex hormones and contraceptives, spermicidal agents, and stimulants (immunostimulating agents). The method of conjugating the multi-arm polyethylene glycol-azido derivative of the present invention with protein, peptide or drug active small molecule, may be as described in patent document CN102108119A, conjugates formed via combination end groups with drug molecules.

Compared with the linear polyethylene glycol, the multi-arm polyethylene glycol-azido derivative has a plurality of end groups, further has a plurality of introduction points of functional groups, may load a plurality of active end groups, not only can increase the load rate of the azido active end groups, but also may enhance the stability and security of the azido groups. Hence, the multi-arm polyethylene glycol-azido derivative of general formula I of the present invention has a greater flexibility and a more wide range of applications, and has a good application prospect in organic synthesis, drug synthesis and medical apparatus, etc.

In addition, the multi-arm polyethylene glycol-azido derivative of the present invention may be reacted with another polymer, in particular reacted with polyethylene glycol alkynyl derivative, to form gel. The release rate of the active ingredient may be controlled by changing the molecular weight or the number of branches of the multi-arm polyethylene glycol-azido derivative.

DETAILED DESCRIPTION OF THE INVENTION

Example 1: Preparation of Four-Arm Polyethylene Glycol-Azido Derivative

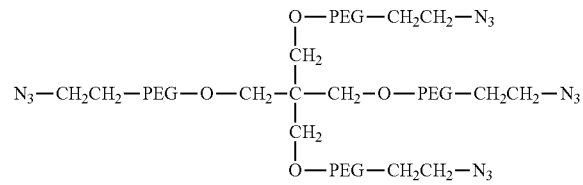

10.0 g of four-arm polyethylene glycol (molecular weight of 5,000) was dissolved in 100 mL of toluene, under nitrogen atmosphere, heated and evaporated 20 mL of toluene, down to room temperature, 10 mL of methylene chloride and 1.45 mL of triethylamine were added, stirred for 10 minutes, 742 μL of methanesulfonyl chloride was added, a sealed reaction overnight, 2 mL of absolute ethanol was added, stirred for 15 minutes, filtered, concentrated to a viscous at 60° C., 150 mL of isopropyl alcohol was heated to dissolve and precipitated with an ice-water bath, filtered, washed the filter cake with isopropanol, dried under vacuum to obtain a four-arm polyethylene glycol sulfonic acid ester.

5.0 g of above four-arm polyethylene glycol sulfonate and 0.52 g of sodium azide (NaN$_3$) were dissolved in 25 mL of N,N-dimethylformamide (DMF), heated to 90° C. and reacted for 2 hours, down to room temperature, 25 mL of water and 5 g of sodium chloride were added, extracted with 25 mL of methylene chloride for three times, combined organic phases, dried with anhydrous sodium sulfate and filtered, concentrated at 50° C., 100 mL of diethyl ether was added to precipitate, the precipitate was collected by filtration and dried under vacuum, the resulting four-arm polyethylene glycol-azido derivative.

IR: 2110 cm$^{-1}$ (—N—N≡N)

Example 2: Preparation of Eight-Arm Polyethylene Glycol-Azido Derivative

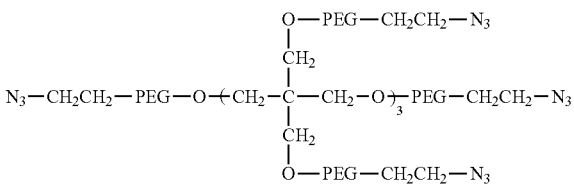

10.0 g of eight-arm polyethylene glycol (molecular weight of 10,000) was dissolved in 100 mL of toluene, under nitrogen atmosphere, heated and evaporated 20 mL of toluene, down to room temperature, 10 mL of methylene chloride and 1.45 mL of triethylamine were added, stirred for 10 minutes, 742 μL of methanesulfonyl chloride was added, a sealed reaction overnight, 2 mL of absolute ethanol was added, stirred for 15 minutes, filtered, concentrated to a viscous at 60° C., 150 mL of isopropyl alcohol was heated to dissolve and precipitated with an ice-water bath, filtered, washed the filter cake with isopropanol, dried under vacuum to obtain the eight-arm polyethylene glycol sulfonic acid ester.

5.0 g of above eight-arm polyethylene glycol sulfonate and 0.52 g of sodium azide (NaN$_3$) were dissolved in 25 mL of N,N-dimethylformamide (DMF), heated to 90° C. and reacted for 2 hours, down to room temperature, 25 mL of water and 5 g of sodium chloride were added, extracted with 25 mL of methylene chloride for three times, combined organic phases, dried with anhydrous sodium sulfate and filtered, concentrated at 50° C., 100 mL of diethyl ether was added to precipitate, the precipitate was collected by filtration and dried under vacuum, the resulting eight-arm polyethylene glycol-azido derivative.

IR: 2110 cm$^{-1}$ (—N—N≡N)

Example 3: Preparation of Four-Arm Polyethylene Glycol-Azido-Mono-Acetic Acid Derivative

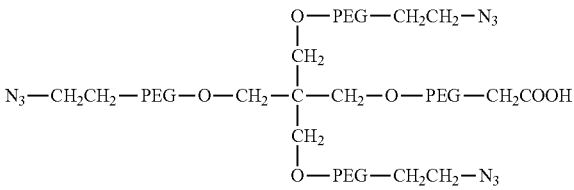

6.0 g of four-arm polyethylene glycol sulfonate-mono-acetic acid methyl ester (molecular weight of 5,000) and 0.468 g of sodium azide (NaN$_3$) were dissolved in 30 mL of N,N-dimethylformamide (DMF), heated to 90° C. and reacted for 2 hours, down to room temperature, 30 mL of water and 7 g of sodium chloride were added, extracted with 30 mL of methylene chloride for three times, combined organic phases, dried with anhydrous sodium sulfate and filtered, concentrated at 50° C., 120 mL of diethyl ether was added to precipitate, the precipitate was collected by filtration and dried under vacuum, the resulting four-arm polyethylene glycol-azido-mono-acetic acid methyl ester.

5.0 g of above four-arm polyethylene glycol azido-mono-acetic acid methyl ester was dissolved in 50 mL of degassed water, 0.5 N aqueous sodium hydroxide to mediate pH 12.0, reacted for 2-2.5 hours at room temperature, 1 N aqueous hydrochloric acid to mediate pH 2-3, 6.0 g of sodium chloride was added, extracted with 50 mL of methylene chloride for three times, combined organic phase, dried with anhydrous sodium sulfate, filtered, concentrated to a viscous at 45° C., 75 mL of diethyl ether was added to precipitate, the precipitate was collected by filtration and dried under vacuum. The resulting four-arm polyethylene glycol-azido-mono-acetic acid derivative.

IR: 2110 cm$^{-1}$ (—N—N≡N)
1H-NMR (DMSO) δ: 4.01 (s, CH$_2$COOH, 2H)

Example 4: Preparation of Four-Arm Polyethylene Glycol-Azido-Mono-NHS Ester Derivative

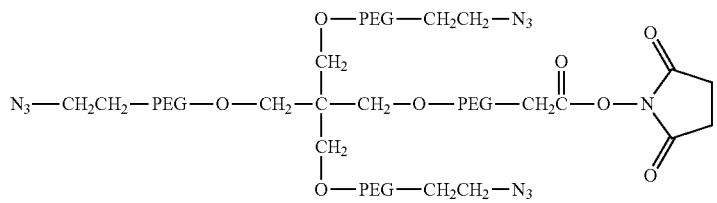

Weighed 1.0 g of four-arm polyethylene glycol-azido-mono-acetic acid (molecular weight of 5,000) and 0.0276 g of N-hydroxy succinimide (NHS), dissolved with 10 mL of methylene chloride, under nitrogen atmosphere, 0.0536 g of N,N'-dicyclohexyl-carbodiimide (DCC) was added, a sealed reaction overnight, filtered, concentrated to dryness at 40° C., 20 mL of isopropanol was heated to dissolve and precipitated with an ice-water bath, filtered, washed the filter cake with isopropanol twice, dried under the vacuum to obtain the four-arm polyethylene glycol-azido-mono-NHS ester derivative.

IR: 2110 cm$^{-1}$ (—N—N=N)
1H-NMR (DMSO) δ: 4.6 (s, CH$_2$CO, 2H), 2.8 (s, CH$_2$ ring, 4H)

Example 5: Preparation of Four-Arm Polyethylene Glycol-Azido-Diacetic Acid Derivative

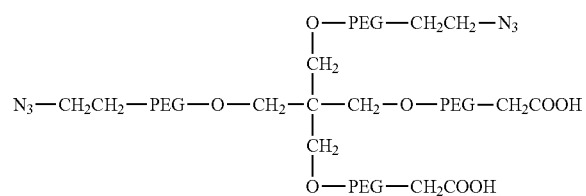

The starting composition is a four-arm polyethylene glycol-sulfonic acid-acetate-diacetic acid methyl ester (molecular weight of about 5,000), the synthetic step is as the same as in example 3.

IR: 2110 cm$^{-1}$ (—N—N=N)
1H-NMR (DMSO) δ: 4.01 (s, CH$_2$COOH, 4H)

Example 6: Preparation of Four-Arm Polyethylene Glycol-Azido-Di-NHS Ester Derivative

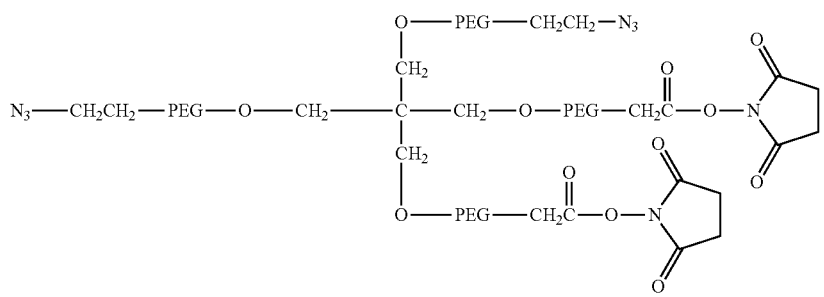

The starting composition is a four-arm polyethylene glycol-azido-diacetic acid (molecular weight of about 5,000), the synthetic step is as the same as in example 4.

IR: 2110 cm$^{-1}$ (—N—N=N)
1H-NMR (DMSO) δ: 4.6 (s, CH$_2$CO, 4H), 2.8 (s, CH$_2$ ring, 8H)

Example 7: Preparation of Four-Arm Polyethylene Glycol-Three-Azido-Mono Amine Derivative

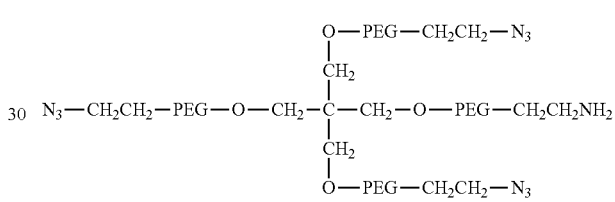

10.0 g of four-arm polyethylene glycol hydroxy-mono-amine (molecular weight of 5,000) was dissolved in 100 mL of methylene chloride, 0.31 mL of triethylamine was added, stirred for 10 minutes, 0.6 mL of di-tert-butyl dicarbonate (Boc$_2$O) was added, reacted overnight at room temperature, concentrated at 45° C., precipitated with 100 mL of diethyl ether, filtered, and dried under the vacuum to obtain the four-arm polyethylene glycol hydroxy-mono-Boc amide.

8.0 g of above four-arm polyethylene glycol hydroxy-mono-BOC amide was dissolved in 80 mL of toluene, under the nitrogen atmosphere, heated and evaporated 15 mL of toluene, down to room temperature, 8 mL of methylene chloride and 0.31 mL of triethylamine were added, stirred for 10 minutes, 0.16 mL of methanesulfonyl chloride was added, a sealed reaction overnight, 0.5 mL of absolute ethanol was added, stirred for 15 minutes, filtered, concentrated to a viscous at 60° C., 120 mL of isopropyl alcohol was heated to dissolve and precipitated with an ice-water bath, filtered, washed the filter cake with isopropanol, dried under vacuum to obtain four-arm polyethylene glycol sulfonate-mono-BOC amide.

5.0 g of above four-arm polyethylene glycol sulfonate-mono-BOC amide and 0.39 g of sodium azide (NaN₃) were dissolved in 25 mL of N,N-dimethylformamide (DMF), heated to 90° C. and reacted for 2 hours, down to room temperature, 25 mL of water and 5 g of sodium chloride were added, extracted with 25 mL of methylene chloride for three times, combined organic phases, dried with anhydrous sodium sulfate and filtered, concentrated at 50° C., 100 mL of diethyl ether was added to precipitate, the precipitate was collected by filtration and dried under vacuum, the resulting four-arm polyethylene glycol-azido-mono-BOC amide.

3.0 g of above four-arm polyethylene glycol-azido-mono-BOC amide was dissolved in 21 mL of methylene chloride, 9 mL of trifluoroacetic acid was added, reacted for 3 hours, concentrated at 45° C., precipitated with 60 mL of diethyl ether, filtered, dried the vacuum to obtain four-arm polyethylene glycol-azido-mono-amine derivative.

IR: 2110 cm⁻¹ (—N—N═N)
1H-NMR (DMSO) δ: 3.0 (m, CH₂NH₂, 2H)

Example 8: Preparation of Four-Arm Polyethylene Glycol-Azido-Mono-Maleimide Derivative

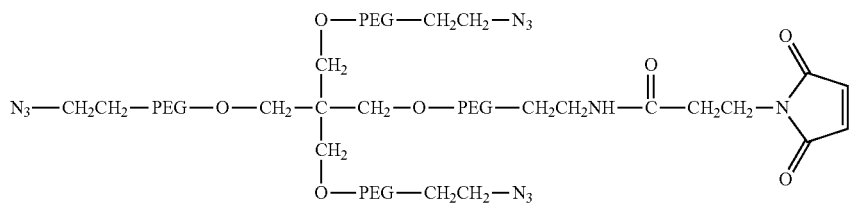

1.0 g of four-arm polyethylene glycol-azido-mono-amine (molecular weight of 5,000) was dissolved in 10 mL of methylene chloride, under nitrogen atmosphere, 0.031 mL of triethylamine was added, stirred for 10 minutes, 0.074 g of MAL-NHS was added, reaction was allowed to proceed overnight protected from light, concentrated to dryness at 40° C., 20 mL of isopropanol was heated to dissolve and precipitated with an ice-water bath, filtered, washed the filter cake with isopropanol twice, dried under the vacuum to obtain the four-arm polyethylene glycol-azido-mono-maleimide derivative.

IR: 2110 cm⁻¹ (—N—N═N)
1H-NMR (DMSO) δ: 2.32 (t,

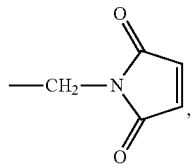

2H), 7.0 (s, CH ring, 2H)

Example 9: Preparation of Four-Arm Polyethylene Glycol-Diazido-Diamino Derivative

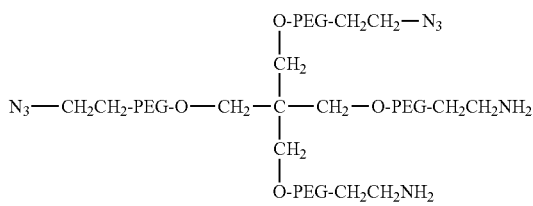

The starting composition is a four-arm polyethylene glycol-hydroxy-diamine (molecular weight of about 5,000), the synthetic step is as the same as in example 7.

IR: 2110 cm⁻¹ (—N—N═N)
1H-NMR (DMSO) δ: 3.0 (m, CH₂NH₂, 4H)

Example 10: Preparation of Four-Arm Polyethylene Glycol-Diazido-Dimaleimide Derivative

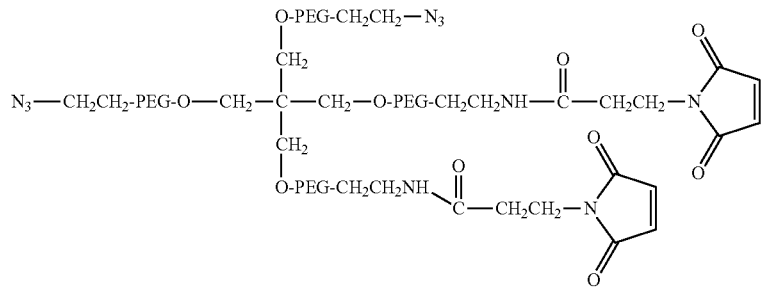

The starting composition is a four-arm polyethylene glycol-azido-diamine (molecular weight of about 5,000), the synthetic step is as the same as in example 8.

IR: 2110 cm$^{-1}$ (—N—N=N)

1H-NMR (DMSO) δ: 2.32 (t,

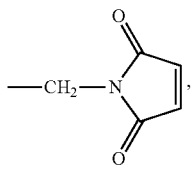

4H), 7.0 (s, CH ring, 4H)

Example 11: Preparation of Eight-Arm Polyethylene Glycol-Seven Azido-Mono-Acetic Acid Derivative

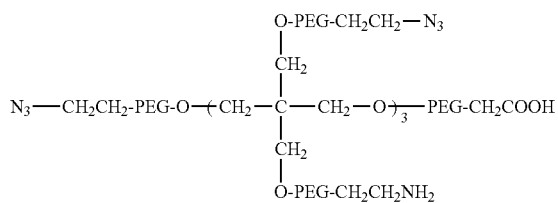

10.0 g of eight-arm polyethylene glycol sulfonate-mono-acetic acid methyl ester (molecular weight of 10,000) and 0.91 g of sodium azide (NaN$_3$) were dissolved in 50 mL of N,N-dimethylformamide (DMF), heated to 90° C. and reacted for 2 hours, down to room temperature, 50 mL of water and 12 g of sodium chloride were added, extracted with 50 mL of methylene chloride for three times, combined organic phases, dried with anhydrous sodium sulfate and filtered, concentrated at 50° C., 200 mL of diethyl ether was added to precipitate, the precipitate was collected by filtration and dried under vacuum, the resulting eight-arm polyethylene glycol-azido-mono-acetic acid methyl ester.

5.0 g of above eight-arm polyethylene glycol-azido-mono methyl acetate was dissolved in 50 mL of degassed water, 0.5 N aqueous sodium hydroxide to mediate pH 12.0, reacted for 2-2.5 hours at room temperature, 1 N aqueous hydrochloric acid to mediate pH 2-3, 6.0 g of sodium chloride was added, extracted with 50 mL of methylene chloride for three times, combined organic phase, dried with anhydrous sodium sulfate, filtered, concentrated to a viscous at 45° C., 75 mL of diethyl ether was added to precipitate, the precipitate was collected by filtration and dried under vacuum. The resulting eight-arm polyethylene glycol-azido-mono-acetic acid derivative.

IR: 2110 cm$^{-1}$ (—N—N=N)

1H-NMR (DMSO) δ: 4.01 (s, CH$_2$COOH, 2H)

Example 12: Preparation of Eight-Arm Polyethylene Glycol-Seven-Azido-Mono-NHS Ester Derivative

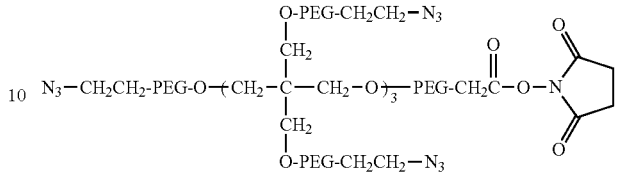

Weighed 2.0 g of eight-arm polyethylene glycol-azido-mono-acetic acid (molecular weight of 10,000) and 0.03 g of N-hydroxy succinimide (NHS), dissolved with 20 mL of methylene chloride, under nitrogen, 0.058 g of N,N'-dicyclohexyl-carbodiimide (DCC) was added, a sealed reaction overnight, filtered, concentrated to dryness at 40° C., 40 mL of isopropanol was heated to dissolve and precipitated with an ice-water bath, filtered, washed the filter cake with isopropanol twice, dried under the vacuum to obtain the eight-arm polyethylene glycol-seven-azido-mono-NHS ester derivative.

IR: 2110 cm$^{-1}$ (—N—N=N)

1H-NMR (DMSO) δ: 4.6 (s, CH$_2$CO, 2H), 2.8 (s, CH$_2$ ring, 4H)

Example 13: Preparation of Eight-Arm Polyethylene Glycol-Seven Azido-Mono-Amine Derivative

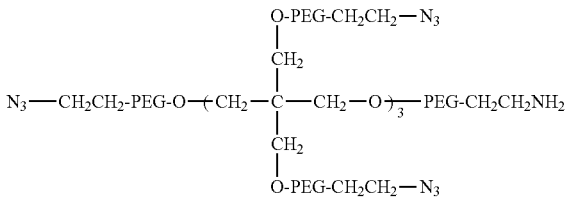

10.0 g of eight-arm polyethylene glycol hydroxy-mono-amine (molecular weight 10,000) was dissolved in 100 mL of methylene chloride, 0.16 mL of triethylamine was added, stirred for 10 minutes, 0.3 mL of di-tert-butyl dicarbonate (Boc$_2$O) was added, reacted overnight at room temperature, concentrated at 45° C., precipitated with 150 mL of diethyl ether, filtered, and dried under the vacuum to obtain the four-arm polyethylene glycol hydroxy-mono-Boc amide.

8.0 g of above eight-arm polyethylene glycol hydroxy-mono-BOC amide was dissolved in 80 mL of toluene, under the nitrogen atmosphere, heated and evaporated 15 mL of toluene, down to room temperature, 8 mL of methylene chloride and 0.16 mL of triethylamine were added, stirred for 10 minutes, 0.08 mL of methanesulfonyl chloride was added, a sealed reaction overnight, 0.5 mL of absolute ethanol was added, stirred for 15 minutes, filtered, concentrated to a viscous at 60° C., 120 mL of isopropyl alcohol was heated to dissolve and precipitated with an ice-water bath, filtered, washed the filter cake with isopropanol, dried under vacuum to obtain eight-arm polyethylene glycol sulfonate-mono-BOC amide.

5.0 g of above eight-arm polyethylene glycol sulfonate-mono-BOC amide and 0.455 g of sodium azide (NaN$_3$) were dissolved in 25 mL of N,N-dimethylformamide (DMF), heated to 90° C. and reacted for 2 hours, down to room temperature, 25 mL of water and 5 g of sodium chloride were added, extracted with 25 mL of methylene chloride for three times, combined organic phases, dried with anhydrous sodium sulfate and filtered, concentrated at 50° C., 100 mL of diethyl ether was added to precipitate, the precipitate was collected by filtration and dried under vacuum, the resulting eight-arm polyethylene glycol-azido-mono-BOC amide.

3.0 g of above eight-arm polyethylene glycol-azido-mono-BOC amide was dissolved in 21 mL of methylene chloride, 9 mL of trifluoroacetic acid was added, reacted for 3 hours, concentrated at 45° C., precipitated with 60 mL of diethyl ether, filtered, dried the vacuum to obtain eight-arm polyethylene glycol-seven-azido-mono-amine derivative.

IR: 2110 cm$^{-1}$ (—N—N=N)
1H-NMR (DMSO) δ: 3.0 (m, CH$_2$NH$_2$, 2H)

Example 14: Preparation of Eight-Arm Polyethylene Glycol-Seven Azido-Mono-Maleimide Derivative

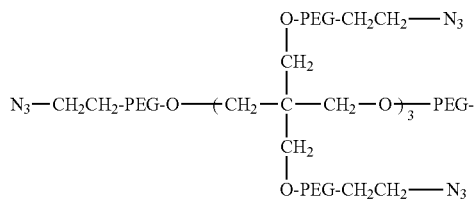

1.0 g of eight-arm polyethylene glycol-azido-mono-amine (molecular weight 10,000) was dissolved in 10 mL of methylene chloride, under nitrogen atmosphere, 0.016 mL of triethylamine was added, stirred for 10 minutes, 0.037 g of MAL-NHS was added, reaction was allowed to proceed overnight protected from light, concentrated to dryness at 40° C., 20 mL of isopropanol was heated to dissolve and precipitated with an ice-water bath, filtered, washed the filter cake with isopropanol twice, dried under the vacuum to obtain eight-arm polyethylene glycol-seven azido-mono-maleimide derivative.

IR: 2110 cm$^{-1}$ (—N—N=N)
1H-NMR (DMSO) δ: 2.32 (t,

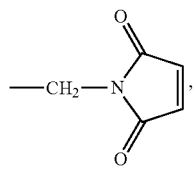

2H), 7.0 (s, CH ring, 2H)

Example 15: Preparation of Click Gel by using a Four-Arm Polyethylene Glycol-Azido (Molecular Weight of 5,000) and the Drug Release Test In Vitro Thereof 0.25 g of four-arm polyethylene glycol-azido (molecular weight of about 5,000), 0.25 g of polyethylene glycol-alkynyl derivatives (molecular weight of about 5,000) and 0.05 g of irinotecan-glycine hydrochloride salt were dissolved in 5 mL of water, 0.008 g of sodium ascorbate and 0.004 g of copper acetate were added, stirred for 25 minutes to form a gel at room temperature.

The above gel placed in a dialysis bag (throttle molecular weight of 5000), washed with 20 mL of water for three times, until detecting no UV absorption in aqueous solution with high performance liquid chromatography (HPLC), put into a glass vial, 20 mL of water was added, shaken at 40° C. in thermostatic oscillatorthe, sampled at 30 min, 2 h, 4 h respectively, 0.0025 g/mL of irinotecan-glycine hydrochloride in water as the reference sample, measured the release amount of the gel at individual time points with high performance liquid chromatography.

The released ratio of Irinotecan-glycine is: 21% at 0.5 hour, 36% at 2 hours, 42% at 4 hours.

Example 16: Preparation of Click Gel by using a Four-Arm Polyethylene Glycol-Azido (Molecular Weight of 10,000) and Drug Release Test In Vitro Thereof 0.25 g of four-arm polyethylene glycol-azido (molecular weight of about 10,000), 0.25 g of polyethylene glycol-alkynyl derivatives (molecular weight of about 10,000) and 0.05 g of irinotecan-glycine hydrochloride salt were dissolved in 5 mL of water, 0.004 g of sodium ascorbate and 0.002 g of copper acetate were added, stirred for 1 hour to form a gel at room temperature.

The above gel placed in a dialysis bag (throttle molecular weight of 5,000), washed with 20 mL of water for three times, until detecting no UV absorption in aqueous solution with high performance liquid chromatography (HPLC), put into a glass vial, 20 mL of water was added, shaken at 40° C. in thermostatic oscillatorthe, sampled at 30 min, 2 h, 4 h respectively, 0.0025 g/mL of irinotecan-glycine hydrochloride in water as the reference sample, measured the release amount of the gel at individual time points with high performance liquid chromatography.

The released ratio of Irinotecan-glycine is: 35% at 0.5 hour, 54% at 2 hours, 69% at 4 hours.

Example 17: Preparation of Click Gel by Using a Eight-Arm Polyethylene Glycol-Azido (Molecular Weight of 10,000) and Drug Release Test In Vitro Thereof 0.25 g of eight-arm polyethylene glycol-azido (molecular weight of about 10,000), 0.25 g of polyethylene glycol-alkynyl derivatives (molecular weight of about 10,000) and 0.05 g of irinotecan-glycine hydrochloride salt were dissolved in 5 mL of water, 0.008 g of sodium ascorbate and 0.004 g of copper acetate were added, stirred for 10 minutes to form a gel at room temperature.

The above gel placed in a dialysis bag (throttle molecular weight of 5,000), washed with 20 mL of water for three times, until detecting no UV absorption in aqueous solution with high performance liquid chromatography (HPLC), put into a glass vial, 20 mL of water was added, shaken at 40° C. in thermostatic oscillatorthe, sampled at 30 min, 2 h, 4 h respectively, 0.0025 g/mL of irinotecan-glycine hydrochloride in water as the reference sample, measured the release amount of the gel at individual time points with high performance liquid chromatography.

The released ratio of Irinotecan-glycine is: 24% at 0.5 hour, 48% at 2 hours, 60% at 4 hours.

Examples 15-17 shows that, in the preparation of gel via a multi-arm polyethylene glycol-azido derivatives reacted with other polyethylene glycol derivatives, the molecular weight and the number of branches of the polyethylene glycol can be used to affect or control the time of gel formation, the lower the molecular weight, the higher the number of the branch, the shorter the time of gel formation, and an increase in the branch number of poly ethylene glycol may be more effective in increasing the gel formation rate. At the same time, the molecular weight and the branch number also have a significant effect on the in vitro drug release time, therefore, to prepare a multi-arm polyethylene glycol-azido derivatives can also be used to control the drug release sustaining process.

Example 18: Preparation of Four-Arm Polyethylene Glycol-Three-Azido-Adamantine and Gel Thereof

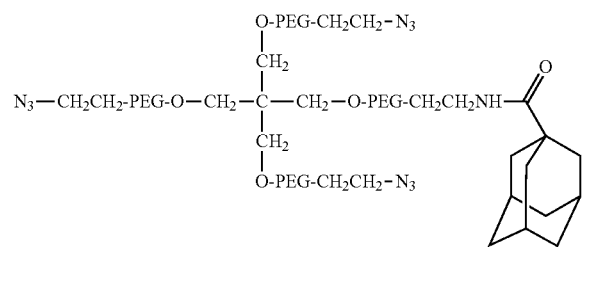

2.0 g of four-arm polyethylene glycol-three-azido-monoamine (molecular weight of 5,000) was dissolved in 20 mL of methylene chloride, 0.12 mL of triethylamine was added, stirred for 10 minutes, 0.23 g of the adamantane-1-carboxamide was added, reaction was allowed to proceed overnight protected from light, concentrated to dryness at 45° C., 40 mL of isopropanol was heated to dissolve and precipitated with an ice-water bath, filtered, washed the filter cake with isopropanol twice, dried under the vacuum to obtain four-arm polyethylene glycol-three azido-adamantane.

IR: 2110 cm$^{-1}$ (—N—N≡N)

1H-NMR (DMSO) δ: 1.6 (m, ring, 6H), 1.7 (m, ring, 6H), 1.9 (m, ring, 3H)

0.33 g of four-arm polyethylene glycol-three-azido-adamantyl (molecular weight of about 5,000) and 0.25 g of polyethylene glycol alkynyl derivatives (molecular weight of about 5,000) were dissolved in 6 mL of water, 0.008 g of sodium ascorbate and 0.004 g of copper acetate were added, stirred at room temperature for 30 minutes to form a gel.

The invention claimed is:

1. A multi-arm polyethylene glycol-adizo derivative having a structure of a general formula I:

wherein:
R is a central molecule and R is pentaerythritol or polypentaerythritol structure, methyl glucoside, sucrose, glycerol or polyglycerol structure;
n is the number of branches or the number of arms, n≥3;
PEG is the same or different —(CH$_2$CH$_2$O)$_m$—, m is an integer of average value of 3-250;
X is a linking group of a azido end group, selected from the group consisting of C$_{1-12}$ alkyl, aryl alkyl, ester group, carbonate group, amide group, amide ester group, ether group, urethane group;
k is the number of the branches having the azido end group, 2≤k≤n;
F is an active end group different from the azido, selected from the group consisting of amino, carboxyl, sulfhydryl, ester group, maleic imide group and acrylic group;
Y is a linking group of an end group F, selected from the group consisting of (CH$_2$)$_i$, (CH$_2$)$_i$NH, (CH$_2$)$_i$OCOO—, (CH$_2$)$_i$OCONH—, (CH$_2$)$_i$NHCOO—, (CH$_2$)$_i$NHCONH—, OC(CH$_2$)$_i$COO—, (CH$_2$)$_i$COO—, (CH$_2$)$_i$CONH; i is an integer of 1-10.

2. The multi-arm polyethylene glycol-adizo derivative of claim 1, wherein, the multi-arm polyethylene glycol-azido derivative having a structure of a general formula II:

R-[-PEG-X—N$_3$]$_k$     (II).

3. The multi-arm polyethylene glycol-adizo derivative of claim 1, wherein, the multi-arm polyethylene glycol-azido derivative having a structure of a general formula III:

4. The multi-arm polyethylene glycol-adizo derivative of claim 1, wherein, R is

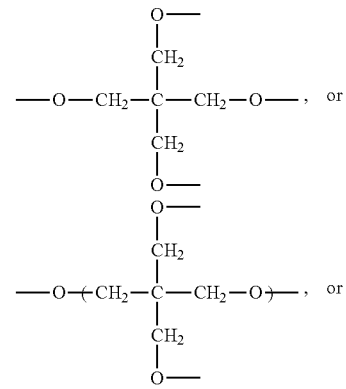

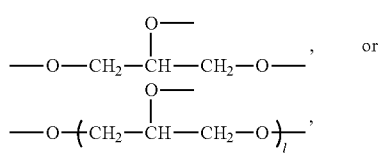

wherein 1 is an integer of ≥1 and ≤10.

5. The multi-arm polyethylene glycol-adizo derivative of claim 1, wherein, 3≤n≤22.

6. The multi-arm polyethylene glycol-adizo derivative of claim 1, wherein, 3≤n≤6.

7. The multi-arm polyethylene glycol-adizo derivative of claim 1, wherein, 2≤k≤16.

8. The multi-arm polyethylene glycol-adizo derivative of claim 1, wherein, k is 2, 4, 6, 8, 10, 12, 14 or 16.

9. The multi-arm polyethylene glycol-adizo derivative of claim 4, wherein, l is 1, 2, 3, 4, 5 or 6.

10. The multi-arm polyethylene glycol-adizo derivative of claim 1, wherein, m is an integer of average value of 68-227.

11. The multi-arm polyethylene glycol-adizo derivative of claim 1, wherein, X is selected from the group consisting of $(CH_2)_i$, $(CH_2)_iNH$, $(CH_2)_iOCOO—$, $(CH_2)_iOCONH—$, $(CH_2)_iNHCOO—$, $(CH_2)_iNHCONH—$, $OC(CH_2)_iCOO—$, $(CH_2)_iCOO—$, $(CH_2)_iCONH$, $(CH_2)_iCOO—$.

12. The multi-arm polyethylene glycol-adizo derivative of claim 1, wherein, Y is selected from the group consisting of $(CH_2)_i$, $(CH_2)_iNH$, $(CH_2)_iCOO—$, $(CH_2)_iCO—$.

13. The multi-arm polyethylene glycol-adizo derivative of claim 11, wherein, i is 1, 2, 3, 4 or 5.

14. The multi-arm polyethylene glycol-adizo derivative of claim 12, wherein, i is 1, 2, 3, 4 or 5.

15. The multi-arm polyethylene glycol-adizo derivative of claim 1, wherein, F is $—NH_2$, $—COOH$, $—OCH_3$,

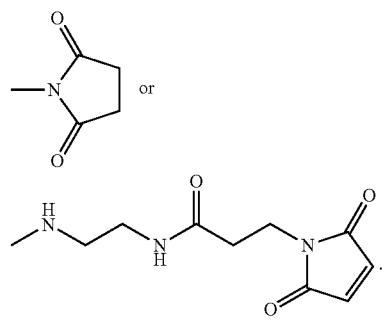

16. The multi-arm polyethylene glycol-adizo derivative of claim 1, wherein, the multi-arm polyethylene glycol-adizo derivative is shown as:

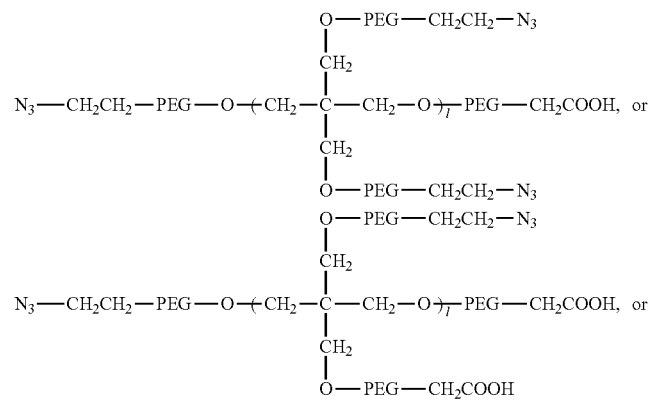

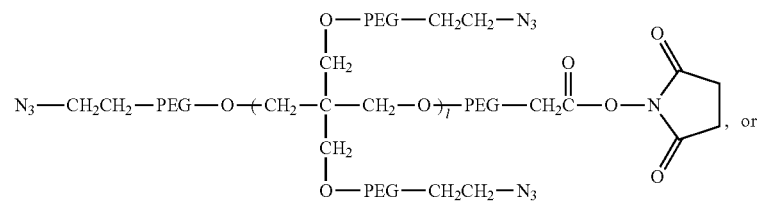

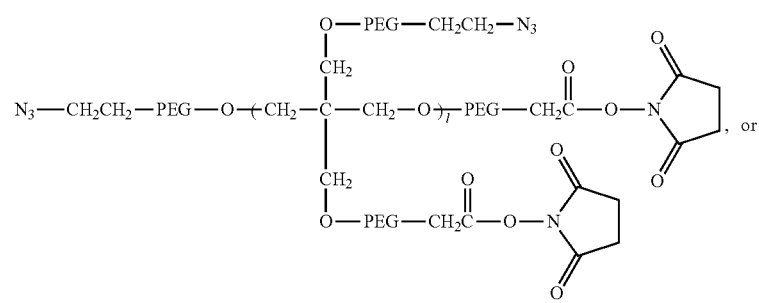

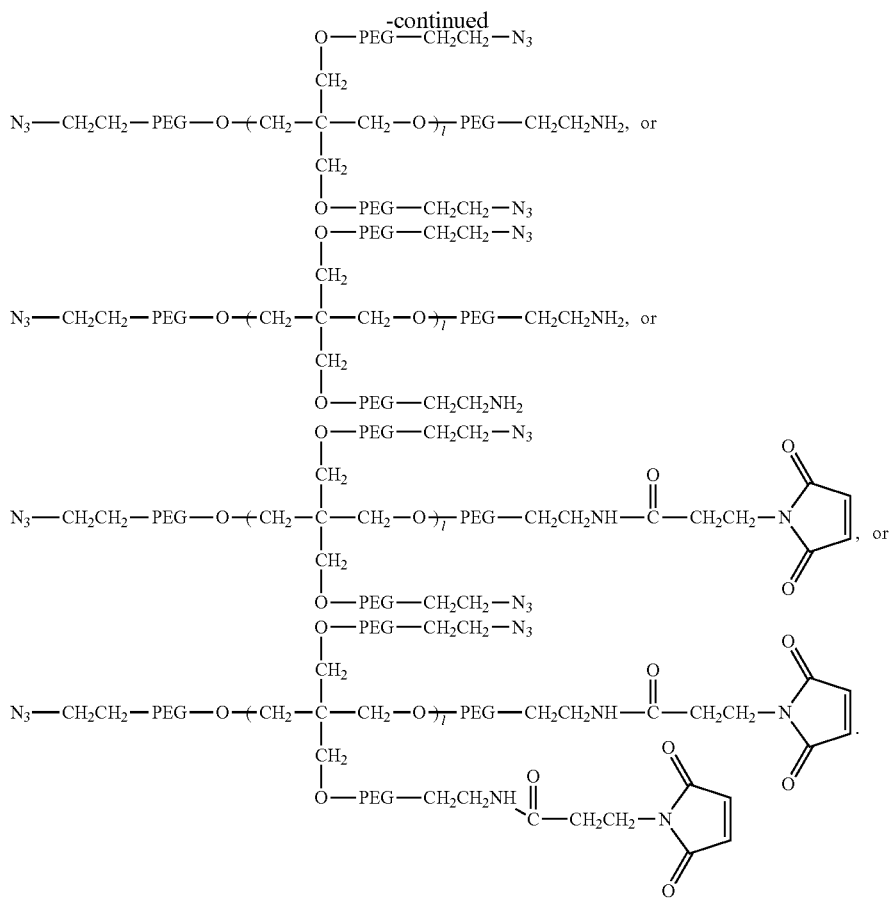

17. A multi-arm polyethylene glycol-adizo derivative, wherein, the multi-arm polyethylene glycol-adizo derivative having a structure of following general formula:

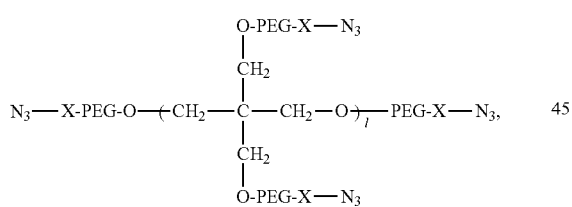

wherein, l is 1, 2, 3, 4, 5 or 6;

X is a linking group of an azido end group, selected from the group consisting of $C_{1-12}$ alkyl, aryl alkyl, ester group, carbonate group, amide group, amide ester group, ether group, urethane group.

18. A multi-arm polyethylene glycol-adizo derivative, wherein, the multi-arm polyethylene glycol-adizo derivative having a structure of following general formula:

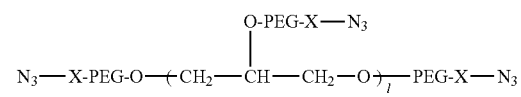

wherein, l is 1, 2, 3, 4, 5 or 6;

X is a linking group of an azido end group, selected from the group consisting of $C_{1-12}$ alkyl, aryl alkyl, ester group, carbonate group, amide group, amide ester group, ether group, urethane group.

* * * * *